(12) United States Patent
Martin

(10) Patent No.: US 8,951,188 B2
(45) Date of Patent: Feb. 10, 2015

(54) ELEMENT FOR TRANSMITTING PULLING AND PUSHING FORCES AS WELL AS TORQUE

(75) Inventor: J. Duncan S. Martin, Scotland (GB)

(73) Assignee: University of Dundee (GB)

(*) Notice: Subject to any disclaimer, the term of this patent is extended or adjusted under 35 U.S.C. 154(b) by 971 days.

(21) Appl. No.: 12/858,151

(22) Filed: Aug. 17, 2010

(65) Prior Publication Data

US 2011/0065516 A1    Mar. 17, 2011

(30) Foreign Application Priority Data

Aug. 17, 2009  (EP) .................................... 09167995

(51) Int. Cl.
- *A61B 1/00* (2006.01)
- *A61B 17/29* (2006.01)
- *F16C 1/04* (2006.01)
- *F16C 1/20* (2006.01)

(52) U.S. Cl.
CPC . *A61B 17/29* (2013.01); *F16C 1/04* (2013.01); *F16C 1/20* (2013.01); *A61B 2017/2902* (2013.01); *A61B 2017/2929* (2013.01)
USPC ................ 600/141; 600/142; 606/1; 606/130

(58) Field of Classification Search
CPC ..................................................... A61B 1/0055
USPC ....................... 138/112, 119, 120; 227/175.1; 600/139–142; 604/528; 606/1, 130, 606/167, 205
See application file for complete search history.

(56) References Cited

U.S. PATENT DOCUMENTS

| | | | | |
|---|---|---|---|---|
| 5,214,970 A | * | 6/1993 | Vezain | 74/18.1 |
| 6,960,163 B2 | * | 11/2005 | Ewers et al. | 600/114 |
| 2005/0096694 A1 | * | 5/2005 | Lee | 606/205 |
| 2005/0103819 A1 | * | 5/2005 | Racenet et al. | 227/175.1 |
| 2005/0250990 A1 | * | 11/2005 | Le et al. | 600/114 |
| 2007/0135803 A1 | * | 6/2007 | Belson | 606/1 |
| 2007/0276430 A1 | * | 11/2007 | Lee et al. | 606/205 |
| 2008/0039690 A1 | * | 2/2008 | Zubiate et al. | 600/141 |
| 2008/0135709 A1 | * | 6/2008 | Zubiate et al. | 248/314 |
| 2008/0163603 A1 | * | 7/2008 | Zubiate et al. | 59/84 |
| 2008/0188891 A1 | | 8/2008 | Frank et al. | |
| 2010/0262180 A1 | * | 10/2010 | Danitz et al. | 606/205 |

FOREIGN PATENT DOCUMENTS

| | | |
|---|---|---|
| DE | 669100 C | 12/1938 |
| GB | 621884 | 4/1949 |
| SU | 1677385 A1 | 9/1991 |

OTHER PUBLICATIONS

European Search Report; Application No. EP 09 16 7995; Jan. 12, 2010; 5 pages.

* cited by examiner

*Primary Examiner* — William Thomson
*Assistant Examiner* — Jeffrey Lipitz
(74) *Attorney, Agent, or Firm* — St. Onge Steward Johnston & Reens LLC

(57) ABSTRACT

An element for transmitting pushing and pulling forces as well as torque having a straight configuration and a bent configuration comprises a base plate, an end plate and bellows arranged between the base plate and the end plate. The base plate and the end plate are connected with a connecting element. A plurality of washers is arranged within the bellows, the washers having a tronconical shape at at least one of their major surfaces. The washers are in mutual contact with each other or with the base plate or the end plate respectively, both in the straight configuration and the bent configuration, such that element can transmit pushing and pulling forces both in the straight configuration and the bent configuration without substantially changing the length of the element.

16 Claims, 3 Drawing Sheets

ELEMENT FOR TRANSMITTING PULLING AND PUSHING FORCES AS WELL AS TORQUE

CROSS-REFERENCE TO FOREIGN APPLICATION

The present application claims priority of European patent application No. 09167995.1 filed on Aug. 17, 2009.

BACKGROUND OF THE INVENTION

The present invention relates to a deflectable element for transmitting pushing and pulling forces as well as torque having a straight configuration and a bent configuration and to a medical instrument comprising such an element.

In medical instruments and in particular in medical instruments for endoscopic surgery it is often necessary to transmit pushing and pulling forces via an actuating element for example from a handle arranged at a proximal end of a medical instrument to a tool or a set of tools at a distal end of the instrument for example in order to open and close the tool. It is often also desirable to transmit torque in order to rotate the tool.

Furthermore the tool is often deflectable relative to the shaft, in which case the instrument must be designed so that the pushing and pulling forces as well as torque can be transmitted both in the deflected and the non-deflected state of the tool.

An element for transmitting torque while in a non-straight configuration is for example known from U.S. Pat. No. 5,214,970. The element disclosed therein comprises a base plate and an end plate and a set of bellows arranged between the base plate and the end plate. Arranged within the set of bellows is a spring which pushes the end plate away from the base plate. Furthermore the element known from this document comprises a wire connecting the base plate to the end plate and limiting the distance by which the base plate and the end plate can be separated from each other.

Although it has been shown that such an element is able to effectively transmit torque as well as, to a certain degree, pulling forces, it has been shown that the transmission of pushing forces using such an element is problematic. If the spring within the element is strong enough to effectively transmit pushing forces it is generally not flexible enough for the element to be bent to any useful degree. If the spring is sufficiently elastic so that the element can be bent to a useful degree, the spring is usually too elastic to transmit pushing forces in any meaningful way or if it does it tends to do so such that the applied forces are transmitted in a non-linear way which is also not desirable.

SUMMARY OF THE INVENTION

It is therefore one aim of the present invention to describe a deflectable element with which pushing and pulling forces as well as a torque can be transmitted in an effective way.

It is a further aim to describe a medical instrument in which a tool can be deflected with regard to a shaft and in which pushing and pulling forces as well as torque can effectively be transmitted from a proximal end of the instrument to a tool at the distal end of the instrument.

According to the invention the problem is solved by a deflectable element for transmitting pushing and pulling forces as well as torque having a straight configuration and a bent configuration comprising a base plate, an end plate, bellows arranged between the base plate and the end plate and a connecting element connecting the base plate with the end plate, whereby a plurality of washers is arranged within the bellows, the washers having a tronconical shape at at least one of their main two surfaces, the washers further being in mutual contact with each other or with the base plate or the end plate respectively, both in the straight configuration and the bent configuration, such that the element can transmit pushing or pulling forces both in the straight configuration and in the bent configuration without substantially changing the length of the element.

The problem is further solved by a medical instrument, preferably an endoscopic instrument comprising an actuating element, whereby the actuating element comprises a deflectable element of the invention.

The term "washer" for the purpose of the present invention refers to any plate-like object having a central hole. Preferably the washers have a circular shape.

The term "main surface" of the washer refers to the two largest surfaces of the washer which are separated from each other by the main body of the washer, i.e. the surfaces usually referred to as the top and the bottom surface of the washer.

The term "tronconical shape" for the purpose of the invention describes any shape of a main surface in which the main surface deviates from the horizontal plane whereby the edge of the respective main surface of the washer is lower compared to the centre of the washer such that the for example a circular washer assumes a flat conical or tronconical shape. Such a shape is sometimes also referred to as a cone or truncated cone shape. The angle of the tronconical shape hereby refers to the angle with which the relevant main surface deviates from the horizontal plane.

The terms "base plate" and "end plate" refer to the two platelike elements which are arranged at the two ends of the bellows and preferably hermetically seal the bellows. The two terms base plate and end plate are merely used to distinguish the two elements and are not meant to indicate a particular preference or orientation.

It has been shown that with a device according to the invention due to the fact that the washers are in contact with each other in both the straight and the bent configuration pushing forces can be transmitted effectively using an element according to the invention.

Furthermore due to the nature of the element the difference in the path length between the base plate and the end plate in the straight configuration and in the bent configuration is very small. Therefore the connecting element can effectively transmit pulling forces both in the straight configuration and the bent configuration without substantially changing the length of the element.

Due to the fact that the base plate and the end plate are connected by bellows, torque can also effectively be transmitted.

In an embodiment the connecting element is a cable preferably a steel cable.

It has been shown that a cable, in particular a steel cable due to its flexibility combined with its high tensile strength is particularly suited for the transmission of pulling forces in the element of the invention while not diminishing the flexibility of the element in any way.

In a further embodiment the washers are made from a polyamide, preferably a nylon.

It has been shown that washers made from a polyamide and in particular from a nylon showed advantageous wear characteristics, especially when used in combination with steel bellows. Therefore the use of such washers leads to elements with a particular long life.

In a further embodiment the bellows are made from metal and preferably from a metal selected from stainless steel and nickel.

In a further embodiment the base plate and the end plate are made from a metal preferably a metal selected independently from stainless steel and nickel.

When the base plate and the end plate or the bellows are made from the above metals an element of particular strength can be obtained. Furthermore, if both plates and the bellows are made from metal they can be welded together and thereby a hermetically sealed element can be obtained which is advantageous for example in medical applications since it is particular easy to sterilize.

In an embodiment the element has an overall length of 15 to 25 mm.

Elements of this size have been proven to be particular useful in medical instruments.

In a further embodiment the plurality of washers comprises 15 to 20 washers.

It has been shown the use of 15 to 20 washers leads to an element which can be bent easily while always maintaining the integrity of the bellows without leading to a massive increase in the overall length of the element.

In a further embodiment the washers have a tronconical shape at only one of their major surfaces.

In this embodiment it is particularly preferred if the washers are stacked in such a way that the surface of a washer having a tronconical shape comes into contact with the surface of a washer which does not have a tronconical shape. The use of washers having a tronconical shape at only one of their major surfaces is advantageous since such washers are particular easy to manufacture.

In a further embodiment of the above measure the angle of the tronconical shape is from 3.5° to 5°.

The use of such an angle is advantageous, since it leads to a useful overall bending angle, which can be achieved without overbending the bellows in the area of contact between the washers.

In further embodiments the washers have a thickness from 0.75 to 1.5 mm.

The use of washers with such thicknesses is preferable since it makes it possible to build elements comprising a number of washers sufficient to avoid overbending the bellows while at the same time not leading to an overly long element.

In a further embodiment the maximum angle of deflection in the bent configuration is from 70° to 90°.

An element that can be bent to a maximum of 70° to 90° has got the advantage that on the one hand a useful deflection is achieved while on the other hand the element does not bend too far so that an effective transmission of torque without damage to the bellows can be ensured.

It is to be understood that the above features and the features yet to be mentioned below can not only be used in the combinations stated but also in other combinations or on their own without departing from the scope of the invention.

The invention is now described in more detail and explained below on the basis of selected exemplary embodiments in conjunction with the accompanying drawings in which:

DETAILED DESCRIPTION OF PREFERRED EXEMPLARY EMBODIMENTS

Figure 1:
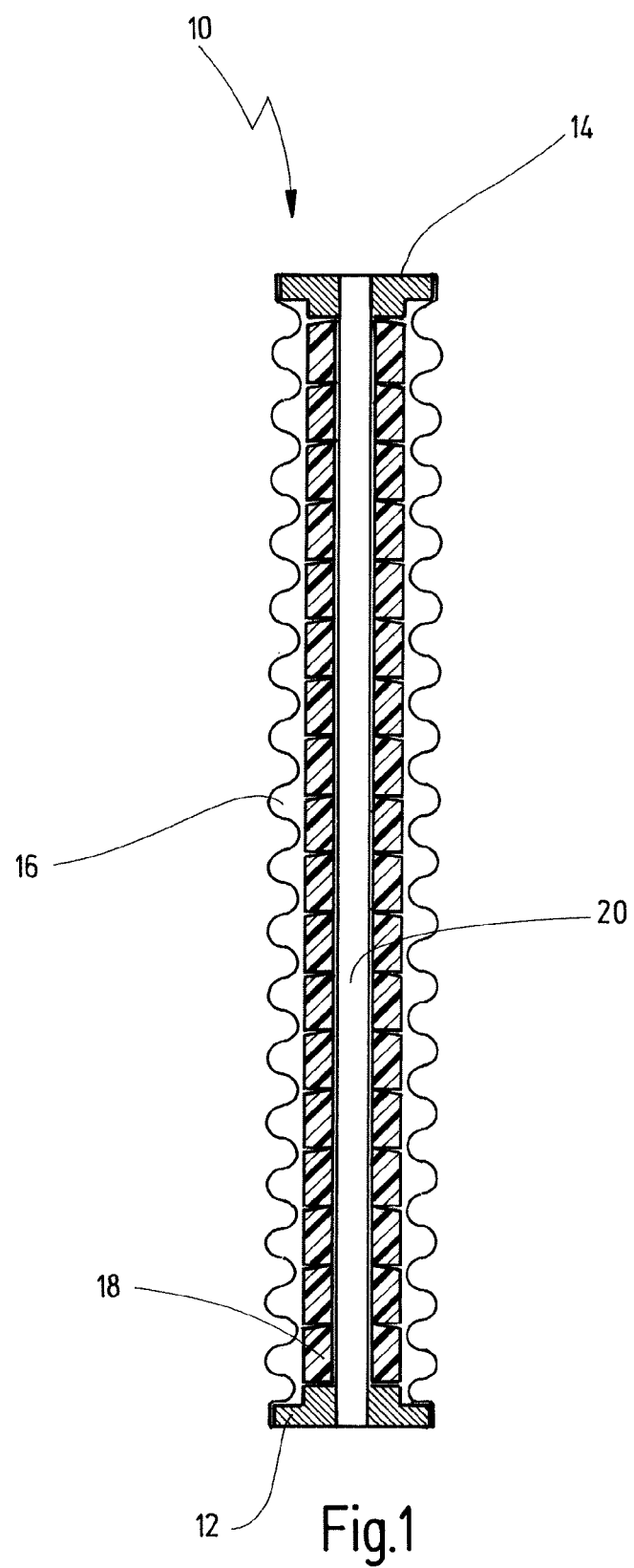
FIG. 1 shows a side view of a deflectable element in straight configuration in section.

In FIG. 1 a deflectable element in its entirety is denoted by the reference numeral 10.

The deflectable element 10 comprises a base plate 12 and an end plate 14 both made from stainless steel. The base plate 12 and the end plate 14 are connected by a set of bellows 16 which are also made from stainless steel and which are connected to the base plate 12 and the end plate 14 by laser welding.

Arranged within the bellows is a plurality of washers of which one exemplarily is denoted with the reference numeral 18. In the present case the deflectable element 10 comprises eighteen washers 18. The washers 18 have a circular shape and are made from nylon.

Furthermore arranged within the bellows 16 and running through the washers 18 is a connecting element in the shape of cable 20. Cable 20 is a 0.5 mm steel cable.

Figure 3:
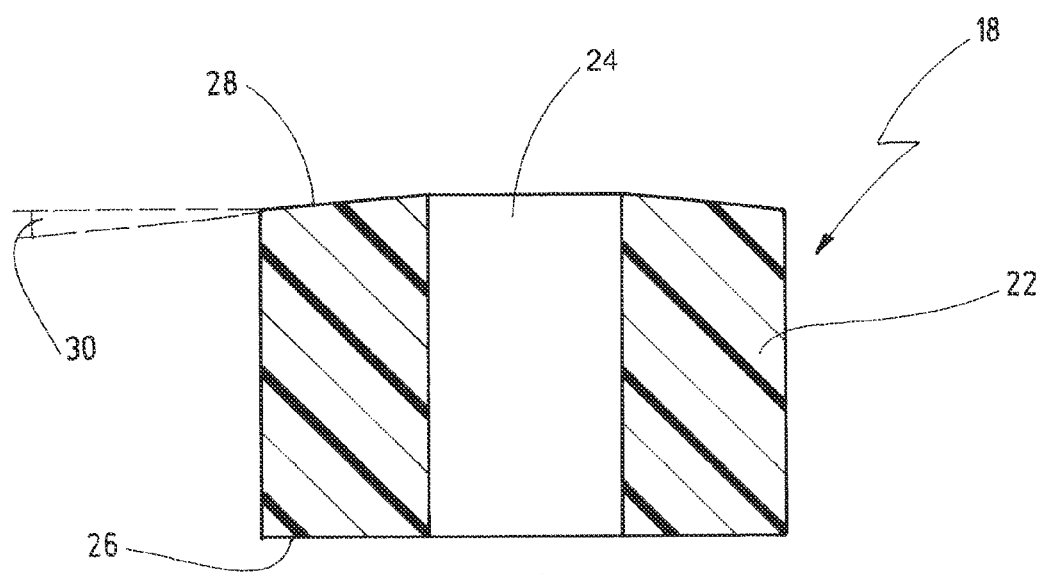
FIG. 3 a side view of a washer of the deflectable element of FIG. 1 in section.

As can be seen in FIG. 3 an individual washer 18 comprises a washer body 22 with a central through bore 24. The washer 22 further comprises two main surfaces, a bottom surface 26 and a top surface 28. As can be seen from this figure the top surface 28 is angled away from the horizontal plane in all directions from the centre of the body 22 of the washer 18. Due to this configuration the washer has at its top surface 28 a very flat tronconical shape. The angle 30 with which the top surface 28 angles away from the horizontal plane which is parallel to the bottom surface 26 is in this case 4.5°.

Figure 2:
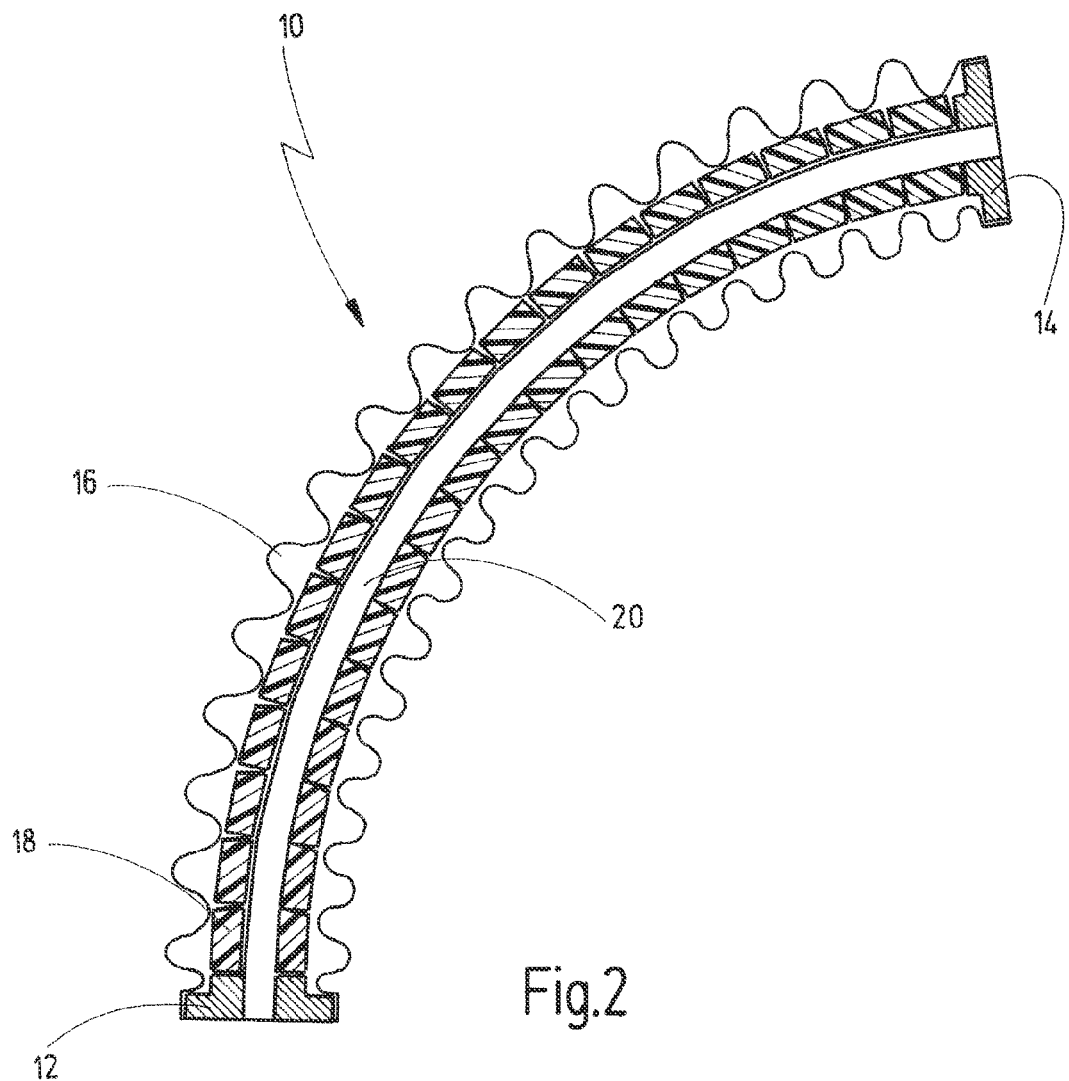
FIG. 2 the deflectable element of FIG. 1 in bent configuration in section.

Due to this shape the washers 18 can be stacked such that they either form a straight stack in which case the through bores 24 form a continuous straight channel as can be seen for example in the straight configuration of the deflectable element 10 as shown in FIG. 1. Furthermore the washers can be arranged such that a bottom surface of one washer 18 comes to lie against the top surface of the other washer 18 such that the contact surface between the two surfaces is maximal. In this case one washer 18 will be angled with respect to the other washer 18. In the present case this angle corresponding to the angle by which the top surface 28 is angled against the horizontal plane is 4.5°. By stacking multiple washers bending angles of multiples of 4.5° can be achieved as seen for example in the bent configuration of the deflectable element 10 shown in FIG. 2. Since in the element 10 eighteen washers 18 are used the overall bending angle is approximately 81°.

It has to be mentioned here that the drawing of the washer in FIG. 3 is not to scale. A washer such as the one displayed in FIG. 3 usually has an overall thickness, i.e. the distance between the bottom surface 26 to the top surface 28 at its maximum of 1 mm, so that the overall length of the element 10 shown in FIGS. 1 and 2 including the thickness of the base on the end plate will be about 20 mm.

Due to the fact that in both the straight configuration and the bent configuration the washers 18 of the element 10 are in contact with each other they are able to effectively transmit pushing forces.

Due to the fact that the base plate 12 and the end plate 14 are connected by the cable 20 and since the length of the channel formed by the through bores 24 of the washers 18 changes only very little between the straight configuration and the bent configuration the element 10 is also able to effectively transmit pulling forces without substantially changing the overall length of the element 10.

Due to the fact that the base plate 12 and the end plate 14 are connected by the metal bellows 16 it is also possible to effectively transmit torque using the element 10 in straight configuration or in bent configuration.

The applicant has performed rotation cycle tests in which the bellows were flexed or bent at 80° and the number of rotations before the bellows collapsed was measured. It was hereby found that an element like the element 10 shown in FIGS. 1 and 2 was able to survive approximately 29,000 rotational cycles whereas a corresponding system without the washers 18 and the cable 20 survived for only 15,260 cycles, i.e. for only about half the number of cycles, showing that the element 10 in addition to the fact that it is suitable for transmitting pushing and pulling forces also shows an enhanced degree of stability when compared to an element not comprising washers 18.

In order to manufacture the element 10 first the base plate 12 is provided and the cable 20 is attached to the centre of the base plate 12. Since both the base plate 12 and the cable 20 are made from stainless steel the attachment is hereby achieved by laser welding but it could also be achieved by other means such as gluing, soldering or other methods known to a man of the art.

In a next step the bellows 16 are attached to the base plate 12 such that the cable 20 runs through the bellows 16 and the bellows 16 are secured to the base plate 12 in this case again by laser welding although other methods are possible. It is even possible to not fixedly connect the base plate 12 and the end plate 14 to the bellows 16 and simply rely on the cable 20 for retaining the integrity of the element 10.

In the next step the washers 18 are inserted into the bellows 16 whereby the cable 20 runs through the through bore 24 of the washers 18. The washers 18 are hereby arranged in such a fashion that every tronconical surface (i.e. here the top surface 28 of the washer 18) of a washer 18 is in contact with a flat surface (i.e. here the bottom surface 26 of the washer 18) of a washer 18.

It is hereby also possible to swap the order of the last two steps mentioned and first thread the washers 18 onto the cable 20 and then insert this assembly into the bellows 16.

In the next step the assembly of base plate 12, washers 18, bellows 16 and cable 20 is deflected such that it reaches its maximum deflection, i.e. the state in which each tronconical surface of each washer 18 is in maximum contact with the flat surface of the washer 18 next to it.

In this state the end plate 14 is arranged on the bellows 16 and the end plate 14 and the bellows 16 are joined together in the present case again by laser welding. The cable 20 is hereby led through a small hole in the centre of the end plate 14.

In the last step the cable 20 is pulled such that the whole assembly is under a small amount of tension and the cable 20 is now connected to the end plate 14 thereby completing the assembly of the element 10.

Figure 4:
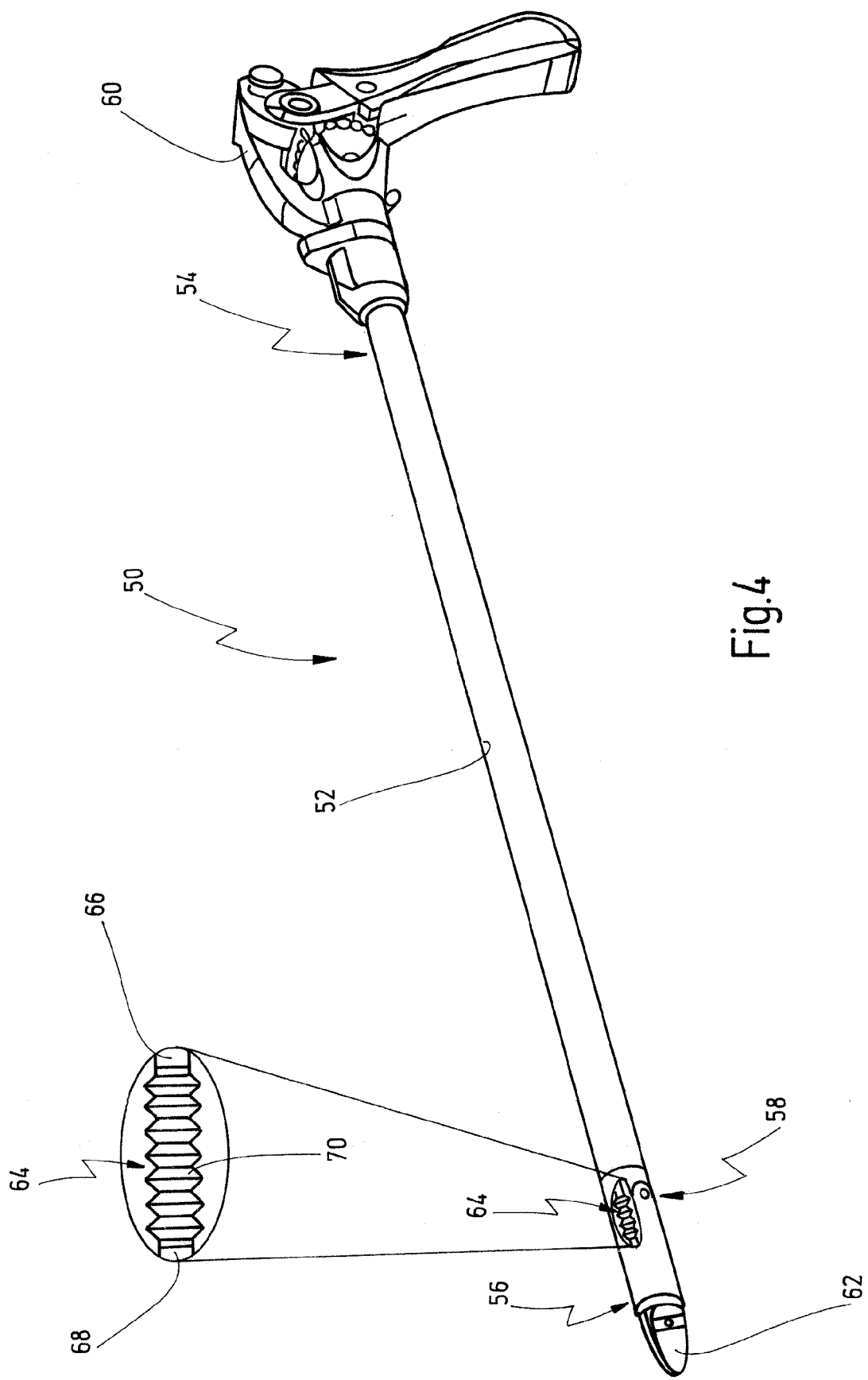
FIG. 4 a side view of a medical instrument partially in section.

In FIG. 4 a medical instrument, in this case an endoscopic instrument is denoted in its entirety by the reference numeral 50.

The medical instrument 50 comprises a shaft 52 having a proximal end 54 and a distal end 56. Arranged between the proximal end 54 and the distal end 56 there is a deflectable section 58 at which the distal end 56 of the shaft 52 can be deflected away from the central axis of the shaft 52.

Arranged at the proximal end 54 of the shaft 52 there is a handle 60 and arranged at the distal end 56 of the shaft 52 there is a tool 62. The handle 60 is in operational connection with the tool 62 by means of an actuating element 64. The part of the actuating element 64 in the area of the deflectable section 58 of the shaft 52 is hereby shown as an enlargement in more detail.

As can be seen from the enlargement the actuating element 64 consists of a first rigid section 66 which runs through the majority of the length of the shaft 52 and is at its most proximal end connected to the handle 60. The actuating element 64 further comprises a second rigid section 68 which runs from the deflectable area 58 to the tool 62. The first rigid section 66 and second rigid section 68 are connected by a deflectable element 70 which is of the same construction as the element 10 shown in FIGS. 1 and 2. Therefore in this medical instrument 50 the handle 60 is in operational connection with the tool 62 whereby the actuating element 64 can transmit pushing and pulling forces from the handle 60 to the tool 62 for example in order to open and close the tool 62. Furthermore the actuating element 64 can transmit torque from the handle 60 to the tool 62 for example in order to rotate the tool 62 around its axis.

In this figure the medical instrument is shown in the non-deflected state, i.e. with the deflectable element 70 in its straight configuration.

If the shaft 52 is deflected at its deflectable section 58 the element 70 moves from its straight configuration to the bent configuration but due to the nature of its construction would still be able to transmit pushing and pulling forces as well as torque from the handle 60 to the tool 62.

What is claimed is:

1. A deflectable element for transmitting pushing and pulling forces as well as torque having a straight configuration and a bent configuration comprising:
   a base plate,
   an end plate,
   bellows arranged between said base plate and said end plate and
   a connecting element connecting said base plate with said end plate, whereby a plurality of washers is arranged within said bellows,
   said washers having a tronconical shape at at least one of their major surfaces,
   said washers further being in mutual contact with each other or with said base plate or said end plate respectively both in said straight configuration and said bent configuration, such that said deflectable element can transmit pushing and pulling forces both in said straight configuration and said bent configuration without substantially changing the length of said deflectable element, said mutual contact configures said washers without penetration into each other, said mutual contact is a direct contact at said at least one of said major surfaces without an intermediate element.

2. The deflectable element of claim 1, whereby said connecting element is a cable.

3. The deflectable element of claim 2, whereby said connecting element is a steel cable.

4. The deflectable element of claim 1, whereby said washers are made from a polyamide.

5. The deflectable element of claim 4, whereby said polyamide is a nylon.

6. The deflectable element of claim 1, whereby said bellows are made from metal.

7. The deflectable element of claim 6, whereby said metal of said bellows is selected from a group consisting of stainless steel and nickel.

8. The deflectable element of claim 1, whereby said base plate and said end plate are made from a metal.

9. The deflectable element of claim 8, whereby said metal of said base plate and said end plate is selected from a group consisting of stainless steel and nickel.

10. The deflectable element of claim 1, whereby said deflectable element has an overall length of 15 to 25 mm.

11. The deflectable element of claim 1, whereby said plurality of washers comprises 15 to 20 washers.

12. The deflectable element of claim 1, whereby said washers have a tronconical shape on only one of their major surfaces.

13. The deflectable element of claim 12, whereby an angle of the tronconical shape is from 3.5° to 5°, said angle measured between a longitudinal axis of said washer and said surface of said tronconical shape.

14. The deflectable element of claim 1, whereby said washers have a thickness from 0.75 to 1.5 mm, said thickness measured between a top surface and a bottom surface.

15. The deflectable element of claim 1, whereby a maximum angle of deflection in said bent configuration is from 70° to 90°.

16. A medical instrument comprising an actuating element, whereby said actuating element comprises a deflectable element of claim 1.

\* \* \* \* \*